US00PP21047P2

(12) United States Plant Patent
Korlipara

(10) Patent No.: US PP21,047 P2
(45) Date of Patent: Jun. 1, 2010

(54) ***COREOPSIS* PLANT NAMED 'SANGRIA'**

(50) Latin Name: ***Coreopsis* sp.**
Varietal Denomination: Sangria

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/321,461

(22) Filed: Jan. 20, 2009

(51) Int. Cl.
*A01H 5/00* (2006.01)

(52) U.S. Cl. ..... Plt./417

(58) Field of Classification Search ..... Plt./417
See application file for complete search history.

*Primary Examiner*—Kent L Bell
(74) *Attorney, Agent, or Firm*—Klarquist Sparkman, LLP

(57) ABSTRACT

A new and distinct *Coreopsis* plant named 'Sangria' characterized by small ruby red inflorescences, and an upright, very dwarf habit.

1 Drawing Sheet

Botanical name: *Coreopsis* sp.
Variety designation: 'Sangria'.

BACKGROUND OF THE INVENTION

The present invention relates to a new and distinct plant of *Coreopsis* and given the cultivar name 'Sangria'. *Coreopsis* is in the family Asteraceae. This new cultivar originated from unknown parents at the nursery in Canby, Oreg. and reproduced in tissue culture where further selections were made. This selection was made for its ruby red inflorescences and compact habit. The species involved are unknown.

SUMMARY OF THE INVENTION

The following traits have been repeatedly observed and are determined to be the unique characteristics of 'Sangria'. These characteristics in combination distinguish 'Sangria' as a new and distinct cultivar:

1. Medium sized, deep ruby red, daisy like, inflorescences.
2. Dwarf upright habit.
3. Very free flowering.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows a one-year-old *Coreopsis* 'Sangria' growing in the ground in the field in August in Canby, Oreg.

DETAILED PLANT DESCRIPTION

The following is a detailed description of the new *Coreopsis* cultivar based on observations of a one-year-old specimen growing in the ground in the trial fields in August in Canby, Oreg. The color descriptions are all based on The Royal Horticultural Society Colour Chart.

Plant:
- *Type.*—Herbaceous perennial.
- *Hardiness.*—USDA Zones 9 to 10.
- *Size.*—25 cm wide and 25 cm tall to top of inflorescences.
- *Form.*—Mound with freely branching stems.
- *Vigor.*—Excellent.

Stem:
- *Type.*—Ascending.
- *Size.*—23 cm tall and 2.5 mm wide.
- *Internode length.*—10 mm to 23 mm.
- *Surface.*—Glabrous.
- *Color.*—Green 137A.

Leaf:
- *Type.*—Simple.
- *Shape.*—Linear, occasionally with 1 narrow pinnae.
- *Arrangement.*—Opposite.
- *Length.*—21 mm to 62 mm, sessile.
- *Width.*—1 mm to 6 mm.
- *Margins.*—Entire.
- *Apex.*—Acute.
- *Base.*—Attenuate.
- *Texture.*—Soft, smooth.
- *Surface texture.*—Glabrous.
- *Venation.*—Pinnate.
- *Color.*—Top side, Green 137A; bottom side Green 137A.

Inflorescence:
- *Type.*—Composite, long stalked terminal heads of daisy type inflorescences.
- *Size.*—25 mm wide and 12 mm deep.
- *Peduncle.*—7 cm high and 1 mm wide, glabrous, Green 137A.
- *Bloom period.*—May through August in Canby, Oreg.
- *Fragrance.*—Light, daisy like.
- *Lastingness.*—Each inflorescence blooms for about a week.
- *Immature.*—6 mm long and 5 mm wide, glabrous, globular, Greyed Green 189A on bottom ⅔ and Greyed Purple 187A on top ⅓.

*Phyllaries.*—In two bowl shaped series; inside series is larger at 10 mm wide and 5 mm deep with 8 reflexed lobes, each 6 mm long and 3 mm wide, shape ovate, margin entire, tip acute, glabrous, both surfaces top half Greyed Yellow 161A with the tip Greyed Orange 166A and bottom half Green 137A; outside series is 5 mm wide and 2 mm deep with 7 to 8 lobes, each 2 mm long and 1.5 mm wide, shape ovate, margin entire, reflexed, tip acute, glabrous, Green 137A.

*Receptacle.*—Bowl shaped, 4 mm wide and 3 mm deep, Green 137A.

*Ray florets.*—8 in number, sterile with no stamen or pistil, obovate with the tip three lobed with lobes obtuse and the central lobe the longest, base attenuate, grows to 10 mm long, 6 mm wide, glabrous on both sides, topside — Deep ruby red, between Greyed Purple 187A and 187B, sometimes lightening toward tip; bottom side — Greyed Red 187C but more blue purple.

*Disc florets.*—About 60 in number, each floret 6 mm long and 0.8 mm wide, tubular, Greyed Purple 187A at the apex to Orange 24A; pistil one in number, 3 mm long, extruding, 2-branched stigma, Orange 24A; stamen 5 in number; pollen Yellow Orange 19A.

*Disc.*—Conic in shape, cone grows to 6.5 mm wide and becoming 3 mm deep with maturity, colored Greyed Red 183A when young, opening to orange, Orange 24A with a dark background, Greyed Red 183A.

Fruit:

*Type.*—Achene, not fully formed.

*Fertility.*—Infertile.

Seed: None produced.

Disease and pests: *Coreopsis* are susceptible to mildew and fungal spots. None of these have been observed on plants grown under commercial conditions in Canby, Oreg.

COMPARISONS TO SIMILAR *COREOPSIS*

Compared to *Coreopsis* 'Limerock Ruby' (U.S. Plant Pat. No. 15,455), this new cultivar has the same inflorescence color but smaller inflorescence size and a much more upright and dwarf habit.

I claim:

1. A new and distinct *Coreopsis* plant herein characterized and described.

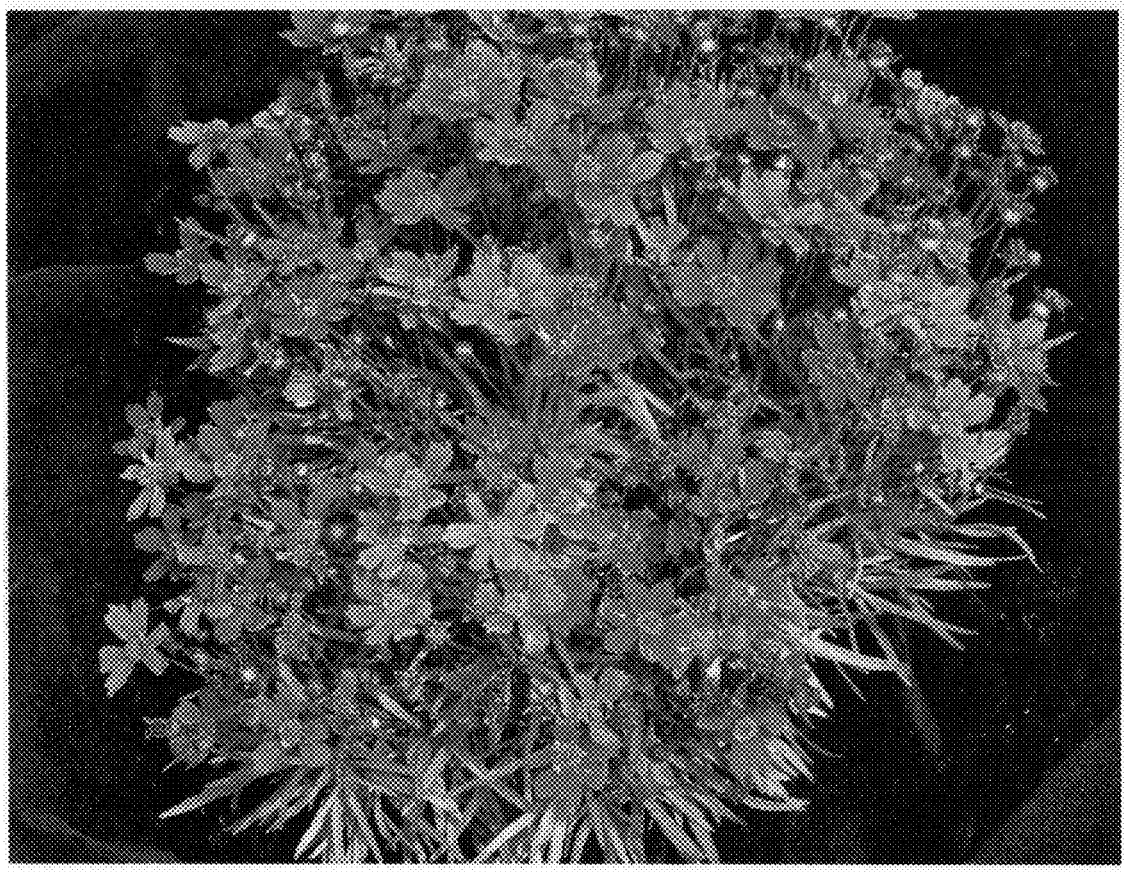

* * * * *